United States Patent [19]

Croze et al.

[11] Patent Number: 5,352,584
[45] Date of Patent: Oct. 4, 1994

[54] MONOCLONAL ANTIBODIES WHICH BIND (E)-5-(2-BROMOVINYL)-ARABINOFURANOSYLURACIL AND DIAGNOSTIC METHODS BASED THEREON

[75] Inventors: Edward M. Croze, San Ramon, Calif.; Jan-I Tu, Lawrenceville; Marc D. Ogan, Somerset, both of N.J.

[73] Assignee: E. R. Squibb & Sons, Inc., Princeton, N.J.

[21] Appl. No.: 468,303

[22] Filed: Jan. 22, 1990

[51] Int. Cl.$^5$ ............... G01N 33/536; G01N 33/543; C07K 15/28; C12N 5/20
[52] U.S. Cl. ............... 435/7.94; 435/240.27; 436/545; 436/548; 436/804; 530/388.9; 530/391.3; 935/100; 935/102; 935/103; 935/104; 935/110
[58] Field of Search ............... 435/7.94, 240.27, 172.2, 435/188; 436/545, 548, 804; 935/100, 102, 103, 104, 110; 530/387, 402, 403, 388.9, 391.3

[56] References Cited

U.S. PATENT DOCUMENTS

| | | | |
|---|---|---|---|
| 4,211,773 | 7/1980 | Lopez et al. | 514/49 |
| 4,367,332 | 1/1983 | Nishimura et al. | 514/49 |
| 4,386,076 | 5/1983 | Machida et al. | 514/50 |
| 4,397,779 | 8/1983 | Groman et al. | 530/403 |
| 4,743,539 | 5/1988 | Gordon et al. | 530/387 |

OTHER PUBLICATIONS

G. Kohler et al., "Continuous Cultures of Fused Cells Secreting Antibody of Predefined Specificity" Nature 256, 495–497 (1975).

Okabayshi, T. et al., Cancer Res., vol. 37 (a), pp. 3132–3135, "A radioimmunoassay for 1-β-D-arabinofuranosyluracil with reference to cross-reactivity of 1-β-D-arabinofuranosylcytosine with an antibody" (1978).

Okabayshi, T. et al., Cancer Res., vol. 37 (2), pp. 625–628, "A radioimmunoassay method for i-β-D-arabinofuranosyluracil using antibodies directed against 1-β-D-arabinofuranosylcytosine" (1977).

*Primary Examiner*—Mary E. Ceperley
*Attorney, Agent, or Firm*—Timothy J. Gaul

[57] ABSTRACT

Monoclonal antibodies which bind (E)-5-(2-bromovinyl)-arabinofuranosyluracil and/or immunologically related compounds, hybrid cell lines which produce these monoclonal antibodies, and immunoassay methods for detecting (E)-5-(2-bromovinyl)-arabinofuranosyluracil and/or immunologically related compounds using these monoclonal antibodies.

30 Claims, 4 Drawing Sheets

| COMPOUND | CROSS-REACTIVITY (%)* | | | |
|---|---|---|---|---|
| | MCBV-1 | MCBV-47 | MCBV-63 | MCBV-157 |
| BV-araU | 100 | 100 | 100 | 100 |
| Bromovinyluracil | >100 | <1.0 | <0.5 | <0.8 |
| uridine | <0.1 | <1.0 | <0.1 | <0.1 |
| uracil | <0.1 | <1.0 | <0.1 | <0.1 |
| arabinose | <0.1 | <0.1 | <0.1 | <0.2 |
| CV-araU | <0.3 | 41 | 35 | 45 |
| uracil-β-D-arabino-furanoside | <0.15 | 9.2 | 2.1 | 4.2 |

* $ED_{50}$ (SQ 32,756) / $ED_{50}$ Cross-reactant x 100

MONOCLONAL ANTIBODIES WHICH BIND (E)-5-(2-BROMOVINYL)-ARABINOFURANOSYLURACIL AND DIAGNOSTIC METHODS BASED THEREON

BACKGROUND OF THE INVENTION

The fusion of mouse myeloma cells to spleen cells derived from immunized mice by Kohler and Milstein in 1975 [Nature 256, 495–497 (1975)] demonstrated, for the first time, that it was possible to obtain continuous cell lines making homogeneous (so-called "monoclonal") antibodies. Since this seminal work, much effort has been directed to the production of various hybrid cell lines (also called "hybridomas") and to the use of the antibodies made by these hybridomas for various scientific investigations. While the general technique for the preparation of hybridomas and monoclonal antibodies is well-known, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity.

The present invention concerns monoclonal antibodies which bind (E)-5-(2-bromovinyl)-arabinofuranosyluracil and/or immunologically related compounds, hybrid cell lines which produce these monoclonal antibodies and immunoassay methods for detecting (E)-5-(2-bromovinyl)-arabinofuranosyluracil and/or immunologically related compounds using these monoclonal antibodies.

SUMMARY OF THE INVENTION

The present invention comprises hybrid cell lines which produce monoclonal antibodies which bind (E)-5-(2-bromovinyl)-arabinofuranosyluracil and/or immunologically related compounds.

The present invention further comprises monoclonal antibodies which bind (E)-5-(2-bromovinyl)-arabinofuranosyluracil and/or immunologically related compounds.

The present invention additionally comprises immunoassay methods for detecting the presence of (E)-5-(2-bromovinyl)-arabinofuranosyluracil and/or immunologically related compounds in a sample.

The present invention also comprises immunoassay methods for quantitatively determining the amount of (E)-5-(2-bromovinyl)-arabinofuranosyluracil and/or immunologically related compounds in a sample.

DETAILED DESCRIPTION OF THE INVENTION

Figure 1:
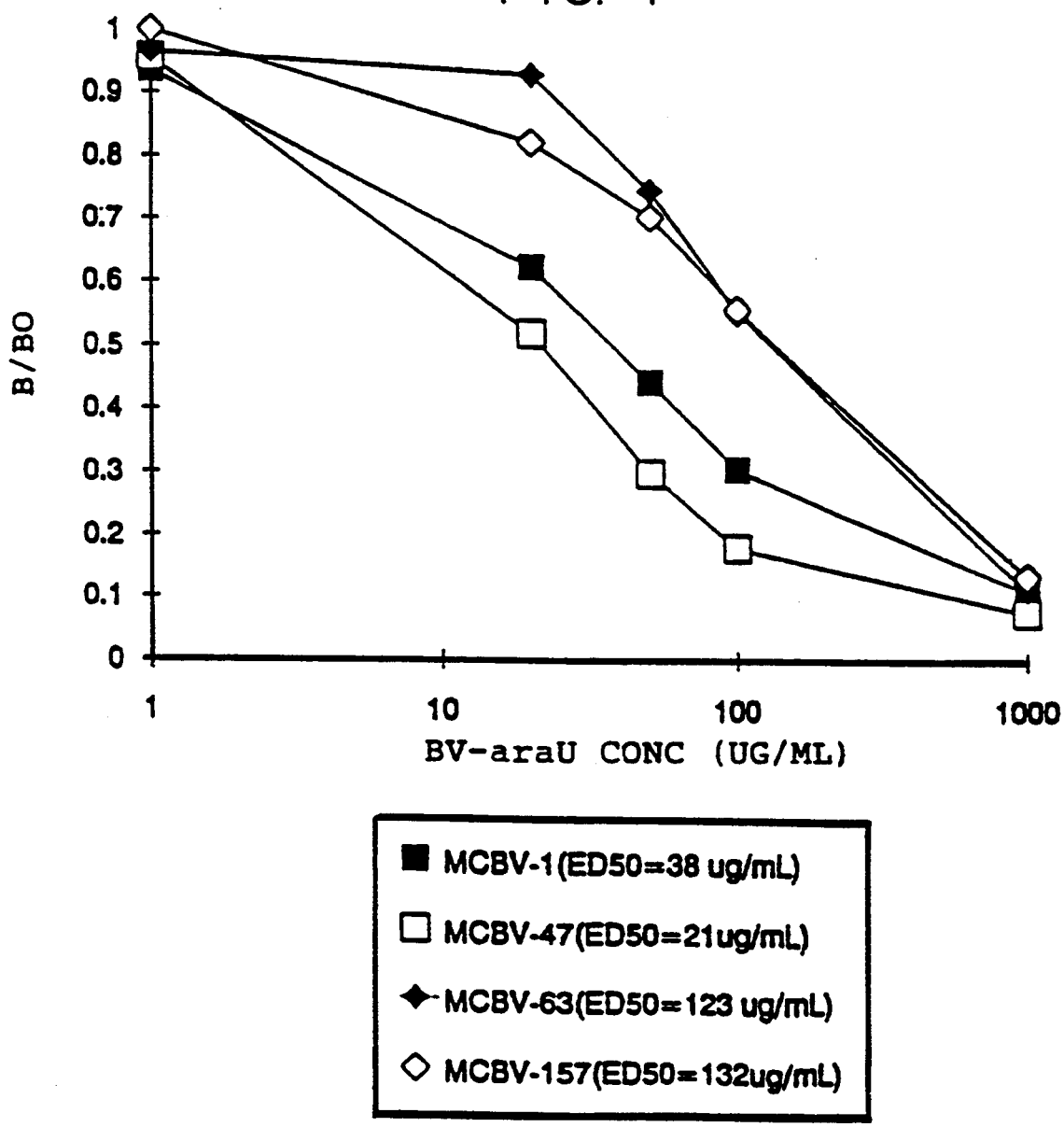
FIG. 1 shows radioimmunoassay standard curves for detecting BV-araU using MCBV-1, MCBV-47, MCBV-63 and MCBV-157.

The present invention concerns hybrid cell lines, also called hybridomas, monoclonal antibodies and immunoassay methods utilizing these antibodies.

In particular, the present invention comprises hybrid cell lines which produce monoclonal antibodies which bind (E)-5-(2-bromovinyl)-arabinofuranosyluracil and/or immunologically related compounds.

As used in this application, the term "immunologically related compounds" means compounds which are capable of being bound by the monoclonal antibodies of the present invention which bind (E)-5-(2-bromovinyl)-arabinofuranosyluracil.

As used in this application, the phrase "(E)-5-(2-bromovinyl)-arabinofuranosyluracil and/or immunologically related compounds", when referring to monoclonal antibodies, means that the monoclonal antibodies are capable of binding only (E)-5-(2-bromovinyl)-arabinofuranosylural, or only compounds immunologically related to (E)-5-(2-bromovinyl)-arabinofuranosyluracil, or both (E)-5-(2-bromovinyl)-arabinofuranosyluracil and immunologically related compounds.

Particularly preferred are hybrid cell lines which produce monoclonal antibodies which bind only (E)-5-(2-bromovinyl)-arabinofuranosyluracil, whose structure is shown in Table 1, and which is sometimes hereinafter referred to as BV-araU.

TABLE 1

STRUCTURES OF BV—araU, IMMUNOGEN-2, RADIOLABEL-2 AND RADIOLABEL-3

| Compound | R |
|---|---|
| BV—araU | —Br |
| Immunogen-2 | —C(=O)—NH-Thyroglobulin |
| Radiolabel-2 | (125I-labeled imidazole structure) |
| Radiolabel-3 | 125I |

Additionally preferred are hybrid cell lines which produce monoclonal antibodies which bind to derivatives or metabolites of BV-araU.

Also preferred are the hybrid cell lines designated as HYBV-1, HYBV-47 (ATCC Accession No. HB10234, American Type Culture Collection, 12301 Parklawn Dr., Rockville, Md. 20852), HYBV-63 and HYBV-157, or hybrid cell lines which have the identifying characteristics of these hybrid cell lines.

Hybrid cell line HYBV-47 was deposited with the American Type Culture Collection, Rockville, Md. on Sep. 22, 1989 under the Budapest Treaty and assigned ATCC accession no. HB 10234.

The hybrid cell lines of the present invention may be produced by various methods generally known to those of ordinary skill in the art. In general, the method involves immunizing suitable mammals, for example mice, with the antigen of interest, in this case BV-araU, fusing antibody producing cells isolated from the animal with myeloma cells, cloning the resulting hybrid cells and selecting those cells which produce the desired monoclonal antibody which binds the antigen of interest.

Immunizations are usually performed with purified antigens. In the case of relatively low molecular weight antigens (haptens) such as BV-araU, immunizations are usually performed using the hapten conjugated to a carrier molecule, for example, heat denatured bovine serum albumin (BSA). Various conjugation procedures may be used to conjugate haptens to carrier molecules. For example, an activated ester of a hapten may be prepared by reacting the hapten with 1-ethyl-3-(3-dimethylaminopropyl)carbodiimide and N-hydroxysuccinimide. The conjugate may then be prepared by reacting the activated ester of the hapten with the carrier molecule in a mildly alkaline solution. Alternatively, glutaraldehyde may be employed to conjugate haptens to carrier molecules.

The usual mammals used for immunizations are mice, especially BALB/c mice, but other mammals and mouse strains may also be employed. The immunizations are performed .in a manner known in the art, such as by administering parenterally, intraperitoneally, intravenously and/or subcutaneously, three to six injections each containing an appropriate amount of purified antigen (i.e., from about 1 $\mu$g to about 50 $\mu$g), at intervals of about one to six weeks, usually together with an adjuvant, for example, complete or incomplete Freund's adjuvant. While immunizations are generally performed in vivo, various in vitro procedures are also known.

Antibody-producing cells of the immunized animals, usually spleen cells, are taken from the animals two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids. Myeloma cells that lack the enzyme hypoxanthine-guaninephosphoribosyl transferase (HGPRT) or the enzyme thymidine kinase (TK) and that, for that reason, do not survive in a selective culture medium containing hypoxanthine, aminopterin and thymidine (HAT medium), may be employed. Myeloma cells and cell lines prepared therefrom that do not survive in HAT medium and do not secrete any immunoglobulins or parts thereof, for example cell lines X63-Ag8.653 and Sp2/0-Ag14, may also be used. Various fusion-promoters, for example, Sendai virus or other paramyxoviruses, optionally in UV-inactivated form, calcium ion, surface-active lipids, such as isolecithin, or polyethylene glycol may also be employed. Myeloma cells are usually fused with a three- to twenty-fold excess of spleen cells from immunized animals in a solution containing from 30 to 50% polyethylene glycol (PEG) having a molecular weight of about 1000 to 4000. Exposure to PEG for about 2 to 3 minutes appears to be optimal to prevent toxicity to cells; temperatures of about 37° are recommended.

After fusion, the cells are partitioned out and cultured in selective HAT medium, with only hybrid cells surviving, since these combine, from the myeloma cells, the ability to grow in vitro and, from the antibody-producing cells of the immunized animals, the missing HGPRT or TK genes and, therewith, the ability to survive in HAT medium.

Suitable culture media for the growth of the hybridoma cells are the customary standard culture media, for example, Dulbecco's Modified Eagles Medium or Roswell Park Memorial Institute (RPMI) 1640 medium containing 10–15% fetal calf serum, supplemented with antibiotics. At the beginning of cell growth, so-called feeder cells, for example normal mouse peritoneal exudate cells, spleen cells, bone marrow macrophages or the like, may be added. At regular intervals, said culture media may be supplemented by selective HAT medium to prevent hybrid cells from being overgrown by ordinary myeloma cells still present after the initial HAT selection process.

The cell culture supernatants of the hybrid cells surviving HAT selection are examined for the presence of the desired monoclonal antibodies. Advantageously, the cell supernatants are tested in an immunoassay, for example, radioimmunoassay or enzyme immunoassay, that demonstrates the binding of monoclonal antibodies to the antigen of interest.

Those hybrid cells which produce antibodies having the desired specificity as well as other desirable characteristics can then be maintained as viable cultures and/or frozen for storage.

The present invention further comprises monoclonal antibodies which bind (E)-5-(2-bromovinyl)-arabinofuranosyluracil and/or immunologically related compounds.

Particularly preferred are monoclonal antibodies which bind only BV-araU.

Additionally preferred are monoclonal antibodies which bind to derivatives or metabolites of BV-araU.

Also preferred are the monoclonal antibodies designated as MCBV-1, MCBV-47, MCBV-63 and MCBV-157, or monoclonal antibodies with the identifying characteristics of these monoclonal antibodies.

Particularly preferred are substantially purified monoclonal antibodies which bind BV-araU and/or immunologically related compounds, in particular the monoclonal antibodies designated as MCBV-1, MCBV-47, MCBV-63 and MCBV-157.

Additionally preferred are derivatives of monoclonal antibodies which bind BV-araU and/or immunologically related compounds, in particular derivatives of the monoclonal antibodies designated as MCBV-1, MCBV-47, MCBV-63 and MCBV-157.

The monoclonal antibodies of the present invention may be produced by various methods generally known to those of ordinary skill in the art. Hybrid cells producing such antibodies may be cultured in vitro and the monoclonal antibodies isolated from the culture supernatants, or may be multiplied in vivo in a suitable mammal, and the monoclonal antibodies isolated from the body fluids of that mammal. If desired, a monoclonal antibody resulting from either of these techniques may be converted into a derivative thereof.

Suitable culture media for in vitro culturing are the customary standard culture media, for example, Dulbecco's Modified Eagles Medium or RPMI 1640 medium containing 10 to 15% fetal calf serum and supplemented with antibiotics.

Large quantities of the desired monoclonal antibodies may also be obtained by multiplying the hybrid cells in vivo. For this purpose, antibody producing hybridomas are inoculated intraperitoneally into syngeneic mammals, and after 1 to 3 weeks, the antibodies are isolated from the ascites fluid of those mammals. For example, hybrid cells originating from BALB/c mice are injected intraperitoneally into BALB/c mice that have previously been pretreated intraperitoneally with a hydrocarbon such as 2,6,10,14-tetramethylpentadecane (pristane) to prevent fluid drainage from the intraperitoneal cavity, and, after 8 to 10 days, ascites fluid is withdrawn from these animals.

The monoclonal antibodies produced in vitro or in vivo may be purified using various methods, for example, gel filtration chromatography, ion-exchange chromatography, DEAE-cellulose chromatography or affinity chromatography. Optionally, selected proteins in the culture supernatants or ascites fluid, including the desired monoclonal antibodies, may be precipitated using specific concentrations of ammonium sulphate or the like before being subjected to chromatography.

If desired, derivatives of the monoclonal antibodies produced either in vitro or in vivo may be prepared.

Derivatives of monoclonal antibodies according to the invention include, for example, fragments, such as Fab, Fab' or F(ab')$_2$ fragments, that retain their specificity for the antigenic determinants of the antigen of interest, radioactively labelled monoclonal antibodies which are labelled, for example, with radioactive iodine ($^{125}$I, $^{131}$I), carbon ($^{14}$C), sulphur ($^{35}$S), tritium ($^3$H) or the like, and monoclonal antibodies conjugated with enzymes such as horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase. Additional derivatives include monoclonal antibodies labeled with fluorescent materials such as fluorescein or rhodamine, and monoclonal antibodies labelled with biotin.

Fragments of monoclonal antibodies according to the invention, for example, Fab, Fab' or F(ab')$_2$ fragments, that retain their specificity for the antigenic determinants of the antigen of interest, may be prepared according to generally known methods, for example, by fragmenting monoclonal antibodies by proteolytic digestion with enzymes such as pepsin or papain and/or by cleavage of disulphide bonds by chemical reduction.

Monoclonal antibodies radioactively labelled with iodine ($^{125}$I, $^{131}$I) may be obtained by iodination, for example, with radioactive sodium or potassium iodide after oxidization with a chemical oxidizing agent, such as sodium hypochlorite, chloramine T or the like, or an enzymatic oxidizing agent, such as lactoperoxidase and glucose oxidase. Radioactively labelled monoclonal antibodies according to the invention may also be prepared by adding, to the culture media for the in vitro culturing, in a known manner, radioactively labelled nutrients containing radioactive carbon ($^{14}$C), tritium ($^3$H), sulphur ($^{35}$S) or the like, for example, L-($^{14}$C)-leucine, L-($^3$H)-leucine or L-($^{35}$S)-methionine, and obtaining the monoclonal antibodies as described above.

Enzyme-conjugated monoclonal antibodies according to the invention may be obtained by various generally known methods, for example, by reacting monoclonal antibodies and the desired enzyme after modification with coupling reagents such as aldehydes, carbodiimides, maleimides, imidates, succinimides and pyridyl disulfides. Specific coupling agents include, for example, glutaraldehyde, periodate, N,N'-o-phenylenedimaleimide, N-(m-maleimidobenzoyloxy)-succinimide, N-(3-(2'-pyridyldithio)-propionoxy)-succinimide or the like.

Various enzyme substrates, for example 5-aminosalicyclic acid, O-phenylenediamine, 3,3'-dimethoxybenzidine, and 2,2'-azino-bis-(3)-ethyl-benzothiazolin-6-sulphonic acid for horseradish peroxidase and p-nitrophenyl phosphate for alkaline phosphatase, may be used in conjunction with the enzyme-conjugated antibodies.

It is contemplated that the present invention encompasses all monoclonal antibodies exhibiting the characteristics of the monoclonal antibodies described herein. It was determined that monoclonal antibodies MCBV-1, MCBV-47, and MCBV-63 belong to the class IgG, while monoclonal antibody MCBV-157 probably belongs to the class IgM, although it may be a dual IgM, IgG secretor. It is contemplated that antibodies having the patterns of reactivity illustrated herein are included within the scope of the present invention regardless of the immune globulin class or subclass to which they belong. For example, a monoclonal antibody exhibiting the characteristics described herein may be of the subclass IgG$_1$, IgG$_2$a, IgG$_2$b, or IgG$_3$, or of classes IgM, IgA, or of other known Ig classes.

Furthermore, since the hybrid cell line produced from a known mouse myeloma cell line and spleen cells from a known species of immunized mouse cannot be further identified except by reference to the antibody produced by the hybrid cell line, it is contemplated that all hybrid cell lines producing antibodies having the reactivity characteristics described above are included within the scope of the present invention.

The present invention further comprises immunoassay methods utilizing monoclonal antibodies and derivatives thereof which bind (E)-5-(2-bromovinyl)-arabinofuranosyluracil and/or immunologically related compounds for the qualitative and quantitative determination of (E)-5-(2-bromovinyl)-arabinofuranosyluracil and/or immunologically related compounds, especially in biological fluids.

Particularly preferred is a qualitative immunoassay method for detecting the presence of (E)-5-(2-bromovinyl)-arabinofuranosyluracil and/or immunologically related compounds in a sample comprising:

(a) incubating the sample with a monoclonal antibody which binds to the (E)-5-(2-bromovinyl)-arabinofuranosyluracil and/or the immunologically related compounds; and (b) detecting the presence of immune complexes formed by the (E)-5-(2-bromovinyl)-arabinofuranosyluracil and/or the immunologically related compounds and the monoclonal antibody.

Additionally preferred is an immunoassay method for quantitatively determining the amount of (E)-5-(2-bromovinyl)-arabinofuranosyluracil and/or immunologically related compounds in a sample comprising:

(a) incubating the sample with a monoclonal antibody which binds to the (E)-5-(2-bromovinyl)- arabinofuranosyluracil and/or the immunologically related compounds;

(b) determining the amount of immune complexes formed by the (E)-5-(2-bromovinyl)-arabinofuranosyluracil and/or the immunologically related compounds and the monoclonal antibody; and (c) correlating the amount of immune complexes formed with the amount of (E)-5-(2-bromovinyl)-arabinofuranosyluracil and/or the immunologically related compounds present in the sample.

As used in this application, the phrase "(E)-5-(2-bromovinyl)-arabinofuranosyluracil and/or immunologically related compounds", when referring to immunoassays, means that the immunoassays are capable of detecting only (E)-5-(2-bromovinyl)-arabinofuranosyluracil, or only compounds immunologically related to (E)-5-(2-bromovinyl)-arabinofuranosyluracil, or both (E)-5-(2-bromovinyl)-arabinofuranosyluracil and immunologically related compounds.

The immunoassay method of the present invention may be a radioimmunoassay (RIA) which utilizes, depending on the particular protocol employed, unlabelled or radioactivity labelled derivatives of monoclonal antibodies which bind (E)-5-(2-bromovinyl)-arabinofuranosyluracil and/or immunologically related compounds, either alone or in combination. In the case where the monoclonal antibody which binds (E)-5-(2-bromovinyl)-arabinofuranosyluracil and/or immunologically related compounds is unlabelled, a different detectable marker, for example, a radiolabelled derivative of (E)-5-(2-bromovinyl)-arabinofuranosyluracil, may be employed. Any of the known modifications of RIA, for example, homogeneous RIA, heterogeneous RIA, competitive RIA, and sandwich RIA, may be employed. Particularly preferred is a competitive, heterogeneous RIA. In the preferred assay, a monoclonal antibody which binds (E)-5-(2-bromovinyl)-arabinofuranosyluracil and/or immunologically related compounds is incubated with a sample and a radiolabelled derivative of (E)-5-(2-bromovinyl)-arabinofuranosyluracil and/or an immunologically related compound. After separating unbound radiolabelled derivative from antibody bound radiolabeled derivative, the amount of antibody bound or unbound radioactivity is measured, and correlated with the amount of (E)-5-(2-bromovinyl-)-arabinofuranosyluracil and/or immunologically related compounds in the sample.

The immunoassay method of the present invention may also be, an enzyme immunoassay (EIA) which utilizes, depending on the particular protocol employed, unlabelled or enzyme-labelled derivatives of monoclonal antibodies which bind (E)-5-(2-bromovinyl)-arabinofuranosyluracil and/or immunologically related compounds, either alone or in combination. In the case where the monoclonal antibody which binds (E)-5-(2-bromovinyl)-arabinofuranosyluracil and/or immunologically related compounds is not enzyme labelled, a different detectable marker, for example, an enzyme-labelled antibody capable of binding to the monoclonal antibody which binds (E)-5-(2-bromovinyl)-arabinofuranosyluracil and/or immunologically related compounds, may be employed. Any of the known modifications of EIA, for example, enzyme-linked immunoabsorbent assay (ELISA), may be employed. Particularly preferred is an indirect ELISA. In the preferred assay, a sample is incubated with a monoclonal antibody which binds BV-araU and/or immunologically related compounds, and BV-araU and/or an immunologically related compound conjugated to a carrier protein and immobilized on a solid support. Any of the common supports used in immunoassays may be employed. Suitable solid supports include, for example, the inner walls of glass tubes and polystyrene based microtiter plates, or solid particles made from various materials such as polypropylene, polystyrene, polyethylene and glass. During this step, some of the monoclonal antibody which binds BV-araU and/or immunologically related compounds becomes bound to the immobilized carrier conjugated BV-araU and/or the immobolized carrier conjugated immunologically related compound. Any substances in the sample which do not bind to the immobilized carrier conjugated BV-araU and/or immunologically related compound (e.g., BV-araU in the sample) during this incubation step are separated from the solid support. The solid support is then contacted with an enzyme-labelled second antibody which is capable of binding to the specific monoclonal antibody which is bound to the immobilized, carrier conjugated BV-araU and/or immunologically related compound. After separation of any unbound enzyme-labelled second antibody from the solid support, the solid support is contacted and incubated with an enzyme substrate capable of reacting with the enzyme of the enzyme-labelled antibody to produce a detectable reaction product. The product of the enzymatic reaction is then measured and correlated with the amount of BV-araU and/or immunologically related compounds in the sample.

The immunoassay method of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection system.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. The amount of antibody which binds (E)-5-(2bromovinyl)-arabinofuranosyluracil and/or immunologically related compounds is typically selected to give 50% binding of detectable marker in the absence of sample. For example, in the preferred RIA, the amount of antibody used is selected to give 50% binding of radiolabelled (E)-5-(2-bromovinyl)-arabinofuranosyluracil and/or immunologically related compound when the assay is performed in the absence of sample (E)-5-(2-bromovinyl)-arabinofuranosyluracil and/or immunologically related compound. Based on a literature value of 1–5 µg antibody per ml of media, if media is used as the antibody source, the amount of antibody used per assay will generally range from about 50 ng to about 250 ng. Typical assay conditions include a temperature range of about 4° C. to about 45° C., preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The immunoassay methods of the present invention are especially useful for monitoring the presence or amount of (E)-5-(2-bromovinyl)-arabinofuranosyluracil or its metabolites in the bodily fluids, for example serum and urine, of a human patient being treated with (E)-5-(2-bromovinyl)-arabinofuranosyluracil.

The monoclonal antibodies of the present invention may also be used to purify (E)-5-(2-bromovinyl)-arabinofuranosyluracil and/or immunologically related compounds. Briefly, monoclonal antibodies which bind (E)-5-(2-bromovinyl)-arabinofuranosyluracil and/or immunologically related compounds may be immobilized on a solid support, and contacted with a material (e.g., solution) containing the (E)-5-(2-bromovinyl)-arabinofuranosyluracil and/or immunologically related compound under conditions permitting the monoclonal antibodies to bind the (E)-5-(2-bromovinyl)-arabinofuranosyluracil and/or immunologically related compound. Any unbound material is separated from the immobilized monoclonal antibodies, and the bound (E)-5-(2-bromovinyl)-arabinofuranosyluracil and/or immunologically related compound eluted from the monoclonal antibodies with a suitable eluant to yield purified (E)-5-(2-bromovinyl)-arabinofuranosyluracil and/or immunologically related compound.

The following examples are further illustrative of the present invention. These examples are not intended to limit the scope of the present invention and provide further understanding of the invention.

EXAMPLE I
Cell Culture

Cell culture media and supplies were obtained from Gibco Laboratories (Life Technologies, Inc., Grand Island, N.Y.) unless otherwise indicated. A BALB/C mouse derived P3X63NS1 (hereinafter "NS1") myeloma hypoxanthine guanine phosphoribosyl transferase (HGPRT) deficient cell line (GMO3573A) was purchased from NIGMS Human Genetic Mutant Cell Repository, Coriell Institute for Medical Research (Camden, N.J.). NS1 cells and selected hybridomas were cultured at 37° C. in a 5% $CO_2$ atmosphere in Dulbecco's Modified Eagles Medium (DMEM) supplemented with 10% fetal calf serum, fungizone (100 μg/l), L-glutamine (0.3 mg/ml) and antibiotics (gentamycin, 0.25 mg/ml; kanamycin, 0.1 mg/ml; penicillin, 100 μU/ml; streptomycin, 0.1 mg/ml)(DMEM complete). Anti-PPLO agent (60 μg/ml final concentration), a tylocine tartrate based material obtained from Gibco, was added to cell culture supernatants to control mycoplasma. After fusion, cells were grown in DMEM complete containing HAT (hypoxanthine, 0.1 mM; aminopterin, 0.1 μM; thymidine, 0.016 mM), including a 10-fold dilution of HCF (hybridoma cloning factor) sold under the trademark ORIGEN by IGEN, Inc. (Rockville, Md.).

EXAMPLE II
Production of Monoclonal Antibodies

Immunizations were performed with one of two different immunogens. The structures of these immunogens (Immunogens 1 and 2) are shown in Tables 1 and 2.

Immunogen-1 was prepared as follows. To a suspension of BV-araU (27.5 mg, 0.08 mmol) in 1.0 ml $H_2O$ was added solid $NaIO_4$ (48.1 mg, 0.23 mmol). BV-araU itself may be prepared according to the methods described in U.S. Pat. No. 4,386,076, the specification of which is incorporated herein by reference. The suspension was protected from light and stirred overnight to afford a colorless solution. An aliquot of this reaction solution (0.5 ml, 0.04 mmol) was added dropwise to a solution of thyroglobulin (32.1 mg, $4.9 \times 10^{-5}$ mmol) dissolved in 2.0 ml of 50 mM HEPES buffer, pH 8.2. The reaction was stirred at 4° C. for 90 minutes, then $NaBH_3CN$ (24.5 mg, 0.39 mmol) was added as a solid and the reaction was stirred for 48 hours. The solution was dialyzed against $4 \times 1$ liter of 50 mM phosphate buffer, pH 7.4 and diluted to a final volume of 10 ml to yield a nominal concentration of 3.2 mg/ml protein. The extent of conjugation, determined by difference UV spectral studies, was found to be 30:1 (BV-araU:-thyroglobulin).

Figure 3:
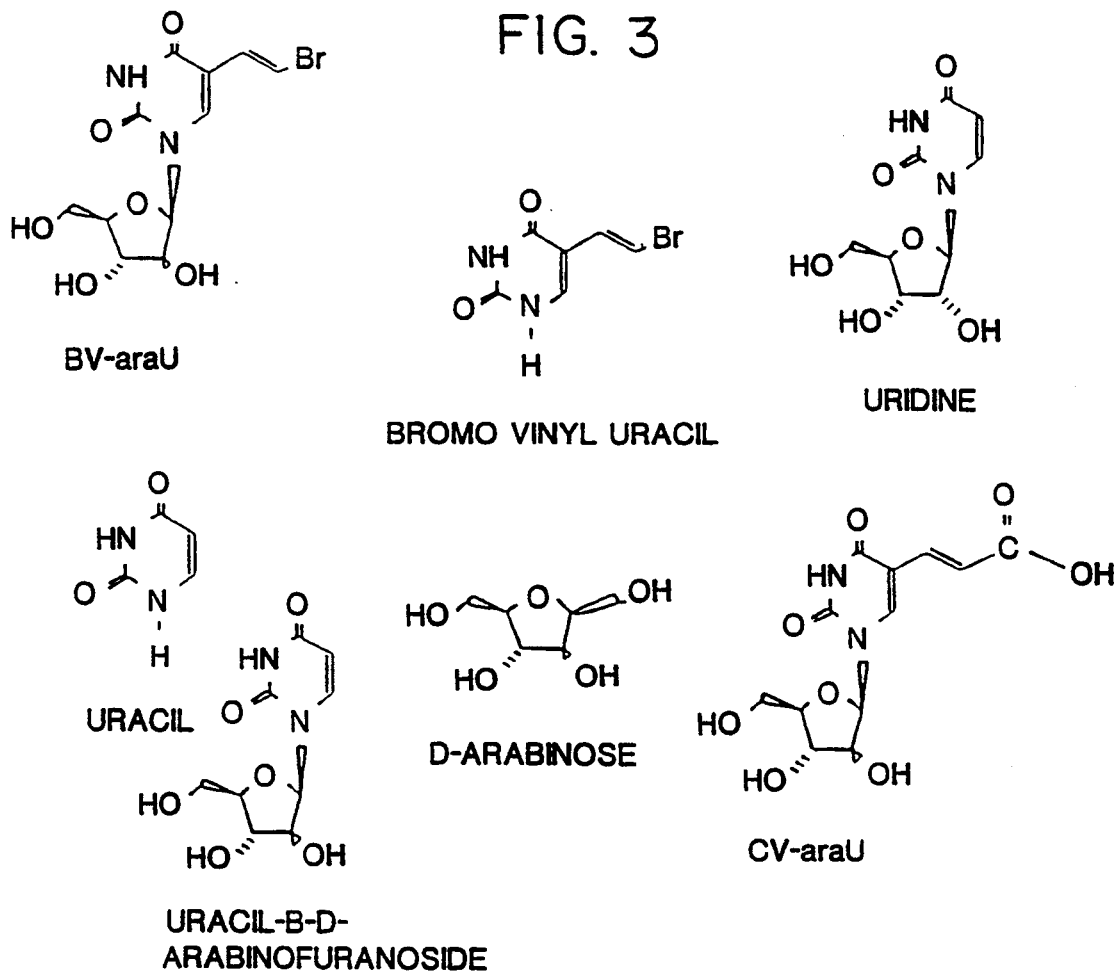
FIG. 3 shows the cross-reactivity of MCBV-1, MCBV-47, MCBV-63 and MCBV-157 with compounds structurally similar to BV-araU by radioimmunoassay.

Immunogen-2 was prepared as follows. To a solution of 3(1-β-D-arabinosfuranosyl-1,2,3,4-tetrahydro-2,4-dioxo-5-pyrimidinyl)-3-propenoic acid (22.7 mg, 0.07 mmol) (CV-araU), the structure of which is shown in FIG. 3, dissolved in 1.0 ml dimethylformamide was added N-hydroxysuccinimide (28.2 mg, 0.25 mmol) and dicyclohexylcarbodiimide (53.0 mg, 0.26 mmol). The resulting solution was stirred under Ar at room temperature for 3 hours to yield the activated ester. An aliquot of the activated ester in dimethylformamide (0.5 ml, 0.04 mmol) was added dropwise to a stirred solution of thyroglobulin (26.4 mg, $4.0 \times 10^{-5}$ mmol) dissolved in 20 ml of 0.1M bicarbonate buffer, pH 8.0. This afforded a milky suspension which was stirred at 4° C. for 24 hours. The suspension was centrifuged and the supernatant was dialyzed against $4 \times 1$ liter of 50 mM carbonate buffer pH 8.0. The extent of conjugation, determined by difference UV spectral studies, was found to be 40:1 (CV-araU:thyroglobulin).

TABLE 2

Structures of Immunogen-1 and
Radiolabel-1

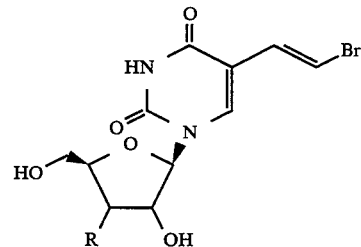

| Immunogen-1 | NH-Thyroglobulin |
| --- | --- |
| Radiolabel-1 | 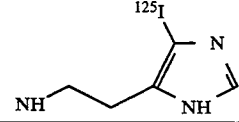 |

Female BALB/c mice were injected with 35 μg of one of the immunogens in a volume of 100 μl. All injections were intraperitoneal using immunogen emulsified for the first dose in complete Freund's adjuvant, and for all subsequent injections in incomplete Freund's adjuvant. Mice, numbers 1 to 5, were immunized with immunogen-1 at 3–4 week intervals for 1 to 3 months. The remaining animals, numbers 6 to 16, were initially immunized with immunogen-1 for 1 month followed by a 2–3 month period during which time they were immunized with only immunogen-2. After immunization, mice were tail bled and the resultant sera analyzed by both RIA and ELISA for the presence of antibodies recognizing BV-araU as described below. Mice having the highest serum titers (those mice whose serum could be diluted 500-fold and still bind greater than 50% of radiolabel, based on the RIA described in Example IV) were selected for fusions. Mice selected for fusion were immunized with 150 μg of carrier-free BV-araU in 100 μl of aseptically filtered 55 mM sodium phosphate buffer, pH 7.3 containing 150 mM NaCl (PBS) for three successive days followed by one day without exposure to BV-araU, just prior to performing a fusion.

Fusions were performed according to a modification of the method of Kohler and Milstein *Nature*, (London) 256: 495–497 (1975), using polyethylene glycol (PEG) 4000 from Gibco. NS1 myeloma cells and spleen cells from selected mice were washed 3 times with DMEM (serum free) and collected by centrifugation. The collected cells were counted, mixed at a ratio of $10^8$ spleen cells to $2 \times 10^7$ myeloma cells in a 50 ml sterile tube and centrifuged for 5 minutes at $450 \times g$. The entire supernatant was removed with a sterile 5 or 10 ml pipette, 1.0 ml of PEG (50% PEG 3,000 to 4,000 in PBS, Gibco Laboratories) was slowly added to the pelleted cells with gentle mixing over 1 minute, and the resulting cell suspension was incubated, while slowly mixing by hand, in a water bath set at 37° C. for 2 to 3 minutes. Serum free DMEM (2.0 ml) was then slowly added to the cell suspension, with mixing, over a 2 to 3 minute period, after which an additional 7.0 ml of DMEM (serum free) was slowly added over 2 to 3 minutes. The cells were then pelleted by centrifugation at $450 \times g$ for 5 minutes. 10 ml of DMEM with 15% horse serum was released directly onto the pellet, and the pellet gently resuspended. 20 ml of DMEM (complete) containing 15% horse serum supplemented with HAT and a 10-fold dilution of HCF (IGEN, Inc.) was then added, and the cells were resuspended, resulting in a cell suspension containing $4 \times 10^5$ myeloma cells/ml in complete media containing HAT and supplemented with HCF to promote cell growth (HAT selection media). Cells were then plated out in 96-well microtiter plates (150 μl/well) by adding to each well 100 μl of cell suspension and 50 μl of DMEM-10% fetal calf serum supplemented with HAT and HCF. The resultant microtiter plates containing the fused cells were placed in a $CO_2$ incubator set at 37° C. After a 24 hour growth period, 100 μl of media was removed from each well and 100 μl of fresh DMEM containing 10% fetal calf serum supplemented with HAT and HCF was added back to each well. Clones growing in selection media in microtiter plate wells were identified by examining each well using an inverted light microscope. Media from wells containing these clones was then tested for the presence of specific antibody by RIA or ELISA.

EXAMPLE III

Expansion of Antibody Producing Hybridomas

Hybridomas producing specific antibody as demonstrated by RIA or EIA were expanded by standard cell culture techniques and gradually transferred, over a period of 3 to 4 weeks, to media containing no aminopterin (HT selection media). Once the hybridomas were completely transferred to HT media, they were gradually transferred, over an additional period of 3 to 4 weeks, to DMEM complete media. Expanded and subcloned hybridomas were grown in DMEM complete media, in T-75 tissue culture flasks (Corning Glass Works, Corning, N.Y.), and media containing antibody harvested when cell growth reached confluency.

When necessary, to obtain high concentrations of antibody, media from T-75 tissue culture flasks was concentrated using an Amicon ultrafiltration unit containing Diaflo XM50 ultrafilters (Amicon).

In addition to cell culture methods, hybridomas were also grown in the peritoneal cavity of syngeneic BALB/c mice. Mice were injected intraperitoneally with 0.5 ml of sterile pristane (2,6,10,14-tetramethypentadecane) (Sigma Chemical Co., St. Louis, Mo.). After 8 to 10 days, hybridomas ($2 \times 10^6$ cells in 100 μl sterile PBS) which were shown by RIA to secrete high concentrations of antibodies recognizing BV-araU (greater than 50% binding of radiolabel using the RIA described in Example IV) were inoculated intraperitoneally into the pristine treated BALB/c mice to produce ascites fluid. Ascites fluid was withdrawn into a sterile Vacutainer containing sodium fluoride (Vacutainer Systems, Rutherford, N.J.) and centrifuged at 2500 rpm for 10 minutes in a Sorvall GLC-1 bench top centrifuge to remove cells. Collected ascites fluid was then tested for the presence of antibody by RIA as described below. Sodium azide (0.2% final concentration) was added to ascites fluid and aliquots (0.5 ml) frozen at $-22°$ C. for long term storage.

EXAMPLE IV

Radioimmunoassay (RIA)

Media containing monoclonal antibody was used to develop a specific RIA for BV-araU. Media (50 μL), assay buffer (150 μL) (50 mM sodium phosphate, pH 6.8, 1.0 mg/ml sodium azide, 1.0 mg/ml EDTA and 1.0 mg/ml bovine serum albumin, fraction V), normal human sera (50 ul) and radiolabel (100 ul, 45,000 CPM) were incubated overnight at 4° C. Standards or cross-reactants (150 uL) were added to each tube in place of assay buffer when constructing a standard curve or determining cross-reactivity. Structures of the cross reactants are shown in FIG. 3. Radiolabel was diluted in assay buffer containing 0.16 mg/ml 8-anilino-1-napthalene sulfonic acid, ammonium salt (ANS) (Aldrich Chemical Company). For screening of HAT selected hybridomas, radiolabel-1 and radiolabel-2, whose structures are shown in Tables 1 and 2, were mixed in equal parts (CPM's) and the resultant mixture used as radiolabel.

Radiolabel-1 was prepared as follows. To a suspension of BV-araU (44.1 mg, 0.13 mmol) in 2.0 ml $H_2O$ was added solid $NaIO_4$ (36.1 mg, 0.17 mmol). The suspension was protected from light and stirred at room temperature overnight to afford a colorless solution. To the solution was then added histamine (39.0 mg, 0.35 mmol). The reaction was stirred for 3 hours, then $NaBH_3CN$ (24.4 mg, 0.39 mmol) was added and the reaction was protected from light and stirred at room temperature overnight. The reaction was subjected to preparative HPLC ($C_{18}$, 2.54×25 cm; 10 mM triethylammonium acetate, pH 7.0/CH$_3$CN (82:18); 15 ml/min, UV 254 nm; t$_r$ 27 to 30 minutes) to afford 11.8 mg of histamine conjugate. A portion of this product was further purified by semi-preparative HPLC (C$_{18}$, 6.8×25 mm; 50 mM triethyl-ammonium acetate, pH 7.0/CH$_3$CN (82:18); 2.0 ml/min, UV 254 nm; t$_r$ 28.5 min) to afford BV-araU histamine conjugate which wad used for radioiodination.

Radioiodination of BV-araU histamine conjugate was achieved as follows. To a solution of BV-araU histamine conjugate (20 µg) dissolved in 20 µl of methanol was added 10 µl (5 mCi) of Na$^{125}$I followed by 20 µl (0.14 µmol) of a 7.1 mM solution of chloramine-T dissolved in phosphate buffer, pH 7.4. After 30 seconds, the reaction was quenched by the addition of 20 µl (0.32 µmol) of a 15.8 mM aqueous solution of Na$_2$S$_2$O$_5$. The reaction was diluted with 100 µl of methanol and subjected to HPLC (C$_{18}$, 4.6×250 mm; 50 mM triethylammonium acetate, pH 7.0/CH$_3$CN (82:18); 1.0 ml/min, radiometric detection; t$_r$ 38.0 min) to afford the desired radiotracer.

Radiolabel-2 was prepared as follows. To a solution of CV-araU (27.1 mg, 0.09 mmol) dissolved in 1.0 ml dimethylformamide was added N-hydroxysuccinimide (18.0 mg, 0.16 mmol) and 1-ethyl-1,3-(3-dimethylaminopropyl)carbodiimide (EDAC) (42.4 mg, 0.22 mmol). The resulting solution was protected from light and stirred under N$_2$ at room temperature for 60 minutes. Histamine (23.1 mg, 0.21 mmol) and Et$_3$N (3 drops) were then added and the reaction was further stirred overnight. The solvent was evaporated under reduced pressure, the residue was dissolved in 2 ml H$_2$O and evaporated to a solid. The solid was dissolved in 3 ml H$_2$O and upon standing afforded crude product as a precipitate. The supernatant was subjected to preparative HPLC (C$_{18}$, 2.54×25 cm; 25 mM NH$_4$OAc, pH 7.0/CH$_3$CN/MeOH (87:7:6); 10 ml/min, UV 254 nm; t$_r$ 18.3 min) to afford CV-AraU histamine conjugate, which was used for radioiodination.

Radioiodination of CV-araU histamine conjugate was achieved as follows. To a solution of CV-araU histamine conjugate (60 µg) dissolved in 20 µl of methanol was added 5 µl (5 mCi) of Na$^{125}$I followed by 20 µl (0.14 µmol) of a 7.1 mM solution of chloramine-T dissolved in 20 mM phosphate buffer, pH 7.4. After 30 seconds, the reaction was quenched by the addition of 20 µl (0.32 µmol) of a 15.8 mM aqueous solution of Na$_2$S$_2$O$_5$. The reaction was diluted with 100 µl of mobile phase and subjected to HPLC (C$_{18}$, 4.6×250 mm; 25 mM NH$_4$OAc, pH 7.0/CH$_3$CN/MeOH (87:8:5); 1.0 ml/min, radiometric detection; t$_r$ 56 min) to afford the desired radiotracer.

Once antibody producing hybridomas were identified, the specificity of the produced antibody for radiolabel-1 or radiolabel-2 was determined. For further assay development, either radiolabel-1 or radiolabel-2 was used with the appropriate antibody.

After incubation, 1.0 ml of PEG 8000 (Fisher Scientific, Fairlawn, N.J.) (25% wt/vol) was added as separatant; samples were centrifuged at 2000×g for 30 minutes at room temperature and the supernatant decanted. Radioactivity associated with the precipitate was then determined using an APEX automatic gamma counter from ICN Micromedic Systems. Satisfactory zero binding and sensitivity were obtained after an overnight incubation at 4° C.

EXAMPLE V

Enzyme-Linked Immunosorbent Assay (ELISA)

Media containing monoclonal antibodies recognizing BV-araU as demonstrated by RIA was also assayed by indirect ELISA. Immunogen-1 or immunogen-2 was diluted in PBS and plated on Immulon-1 96-well polystyrene microtiter plates (Dynatech Laboratories, Inc., Alexandria, Va.) at various concentrations (0-6.0 ug/well) in a volume of 30 µl To maximize binding of the immunogens to each well, the plates were incubated for 1 hour to dryness in an oven set at 50° C. Each well of the microtiter plate was then filled with 300 µl of 55 mM Tris-HCl, pH 7.8, containing 150 mM NaCl and 0.2% gelatin (bloom 300) (Sigma Chemical Co.) and allowed to stand for 30-60 minutes at room temperature. Media (100 µl) containing either MCBV-1, MCBV-47 (1:8 dilution), MCBV-63 (1:1 dilution), or MCBV-157 (1:1 dilution) was added to selected microtiter plate wells, and the plates covered with parafilm and incubated overnight at 4° C. After decanting the media and washing the plates 8 to 10 times with TBS—0.2% gelatin, 100 µl of an affinity purified goat anti-mouse IgG (H+L) horseradish peroxidase (HRP) conjugated antibody (1:500 dilution in TBS) (Organon Teknika-Cappel, Malvern, Pa.) was added to each well followed by a 3 hour incubation at room temperature. Each well of the plates was then washed 8 to 10 times with about 150-200 µl of TBS—0.2% gelatin, 2 times with about 150 to 200 µl of TBS containing 0.1% Tween 20, and once with 0.1M citrate, pH 4.1. The colorimetric product was visualized by adding 100 µl of a substrate solution containing 0.5 mg/ml ABTS 2,2'-azino-bis(3-ethylbenzthiazoline-6-sulfonic acid) (Sigma) and 0.01% H$_2$O$_2$ in 0.1M citrate buffer, pH 4.1 to each well. After 15 minutes, the reaction product was measured at 410 nm using a Dynatech MR 700 microtiter plate reader (Dynatech Laboratories, Inc., Chantilly, Va.).

In order to assay samples thought or known to contain BV-araU, the same procedure is used except that sample is also added with the antibody to the microtiter plate before the overnight incubation at 4° C.

EXAMPLE VI

Sub-Isotyping

To determine the immunoglobulin class/subclass type of monoclonal antibodies recognizing BV-araU, antibody containing media was assayed with an ELISA based procedure following the protocol accompanying a Mouse-Typer Sub-Isotyping Kit (BIO-RAD Isotyping panel 172-2055, Bio-Rad Laboratories, Hercules, Calif.).

EXAMPLE VII

Identification and Characterization of Monoclonal Antibodies Recognizing BV-araU BALB/c mice were shown to have positive serum titers for BV-araU three months after the initial immunization. Of the animals immunized, eleven had greater than 50% binding of radiolabel using a 1:1000 dilution of serum. A total of thirteen fusions were performed and HAT selected hybridomas producing monoclonal antibodies recognizing BV-araU were identified by RIA. Selected hybridomas were expanded, subcloned twice by limiting dilution and their radiolabel specificity determined. MCBV-47, MCBV-63, and MCBV-157 recognized specifically radiolabel-2 whereas MCBV-1 recognized predominantly radiolabel-1.

The class/subclass and light chain designation of each monoclonal antibody was also determined. All monoclonal antibodies contained kappa light chains. MCBV-1, MCBV-47 and MCBV-63 were shown to be of the $IgG_1$, $IgG_{2b}$ and $IgG_1$ subclasses, respectively. MCBV-157 produced a strong signal for IgM in addition to a weak but reproducable signal for $IgG_1$. Although the hybridoma producing MCBV-157 has been subcloned twice by limiting dilution, the possibility cannot be ruled out that this is a mixed clone or dual secretor.

EXAMPLE VIII

Standard Curve For RIA

A standard curve based on a competitive RIA was constructed for each monoclonal antibody as described above. The $ED_{50}$ for each monoclonal antibody was calculated using ISO-DATA 500/100 software (ISO-DATA, Inc. Rolling Meadows, Ill.) pre-programed for use with an APEX Automatic Gamma Counter (ICN Micromedic Systems). Standard curves for each monoclonal antibody and their corresponding $ED_{50}$ values are shown in FIG. 1. The monoclonal antibodies have $ED_{50}$ values which range from 21 to 132 μg BV-araU/ml.

To try to improve the sensitivity of the RIA, a third radiolabel (radiolabel-3) was tested using ascites fluid containing MCBV-47. This radiolabel, $^{125}$I-iodovinylarabinosouracil, the structure of which is shown in Table 1, closely resembles the parent compound, BV-araU. In addition, this label lacks any occurring bridging structure resulting from the conjugation of BV-araU to thyroglobulin.

Radiolabel-3 was prepared as follows. To a solution of CV-araU (58 μg) dissolved in 20 μl of dimethylformamide was added 5 μl (5 mCi) of $Na^{125}I$ followed by 20 μl (0.14 μmol) of a 7.1 mM solution of chloramine-T dissolved in dimethylformamide. After 60 seconds, the reaction was quenched by the addition of 20 μl (0.32 μmol) of 15.8 mM $Na_2S_2O_5$, 20 mM phosphate buffer, pH 7.4. The reaction was diluted with 100 μl of mobile phase and subjected to HPLC ($C_{18}$, 4.6×250 mm; 25 mM $NH_4OAc$, pH 7.0/$CH_3CN$/MeOH (87:8:5); 1.0 ml/min radiometric detection; $t_r$ 56 min) to afford the desired radiotracer.

Figure 2:
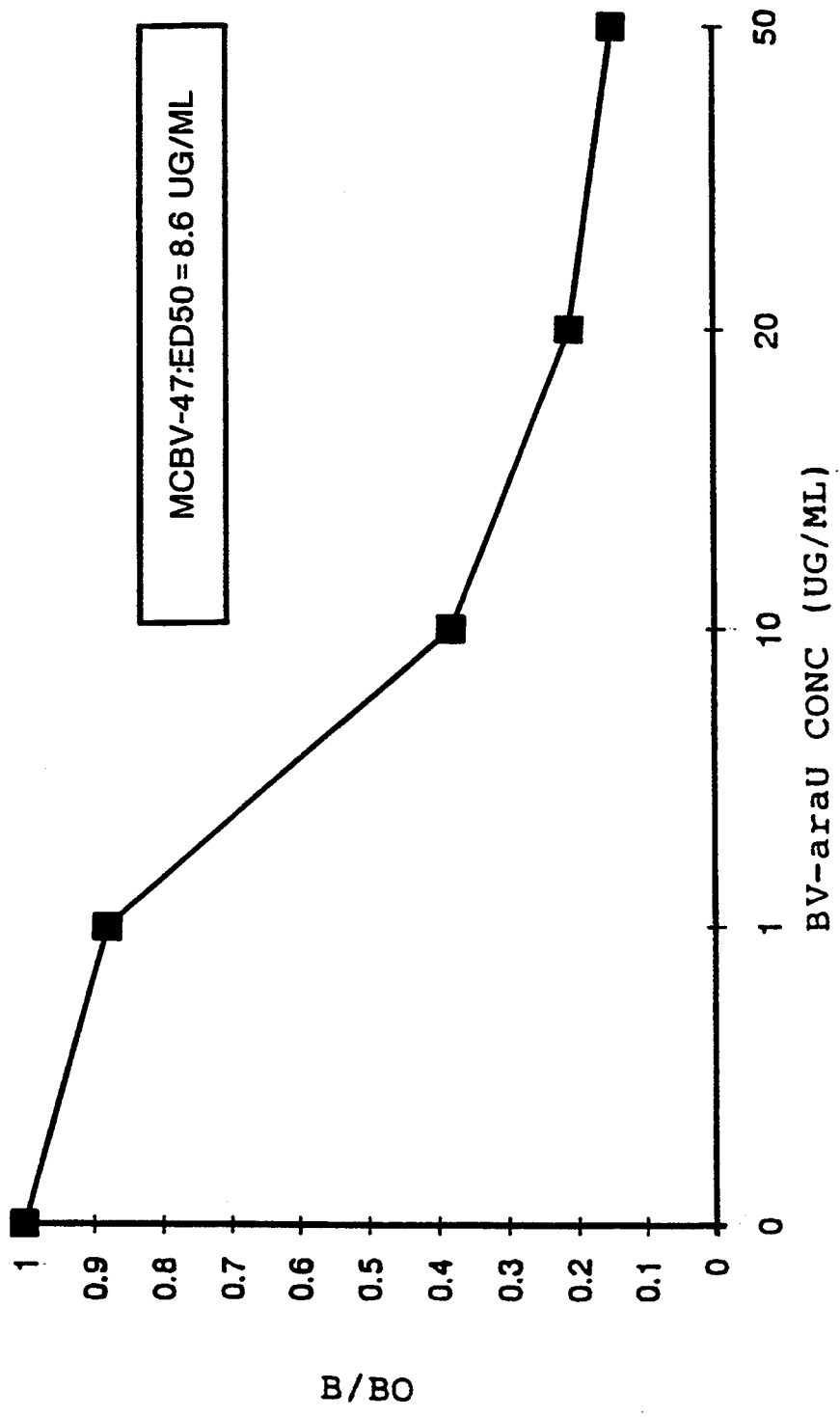
FIG. 2 shows a standard curve for the assay of BV-araU using MCBV-47 and radiolabel-3.

Using radiolabel-3, a decrease in binding of radiolabel resulted as judged by RIA. To compensate for this loss of binding, it was necessary to use high concentrations of ascites fluid to achieve 50% binding of radiolabel-3. Using an appropriate dilution of ascites fluid (1:2), a standard curve for BV-araU was produced using radiolabel-3 and ascites fluid containing MCBV-47 (FIG. 2). By making use of radiolabel-3, the $ED_{50}$ was lowered to 8.6 μg/ml as compared to 21 μg/ml when using radiolabel-2. By utilizing a radiolabel structurally similar to the parent compound BV-araU, it was thus possible to increase the sensitivity of the RIA more than 2-fold.

EXAMPLE IX

Cross-reactivity for RIA

The cross-reactivity of MCBV-1, MCBV-47, MCBV-63, and MCBV-157 with various compounds related to BV-araU was also examined. The structures of these compounds and the results obtained are shown in FIG. 3.

Based on competitive radioimmunoassay, MCBV-1, MCBV-47, MCBV-63 and MCBV-157 all recognize BV-araU.

MCBV-1, which is specific for radiolabel-1, also binds to a potential metabolite of BV-araU, 5-bromovinyluracil (BV-U), but does not bind to a derivative of BV-araU in which the bromide group is replaced with a carboxy group (CV-araU). These results demonstrate that for this monoclonal antibody, the integrity of the arabinose sugar moiety is not necessary for immunogenicity but the presence of the bromovinyl group is.

MCBV-47, MCBV-63 and MCBV-157 bind only radiolabel-2 and do not recognize BV-U. However, these antibodies cross-react partially with CV-araU and uracil-β-D-arabinofuranoside, which are both structurally similar to BV-araU. For MCBV-47, MCBV-63 and MCBV-157, antibody recognition of CV-araU in association with the observed cross-reactivity with uracil-B-D-arabinofuranoside suggests that optimal antibody binding required both the arabinofuranoside, and either the bromovinyl or carboxyvinyl group substitution at position 5 on the pyrimidine.

EXAMPLE X

Characteristics of ELISA

Figure 4A:
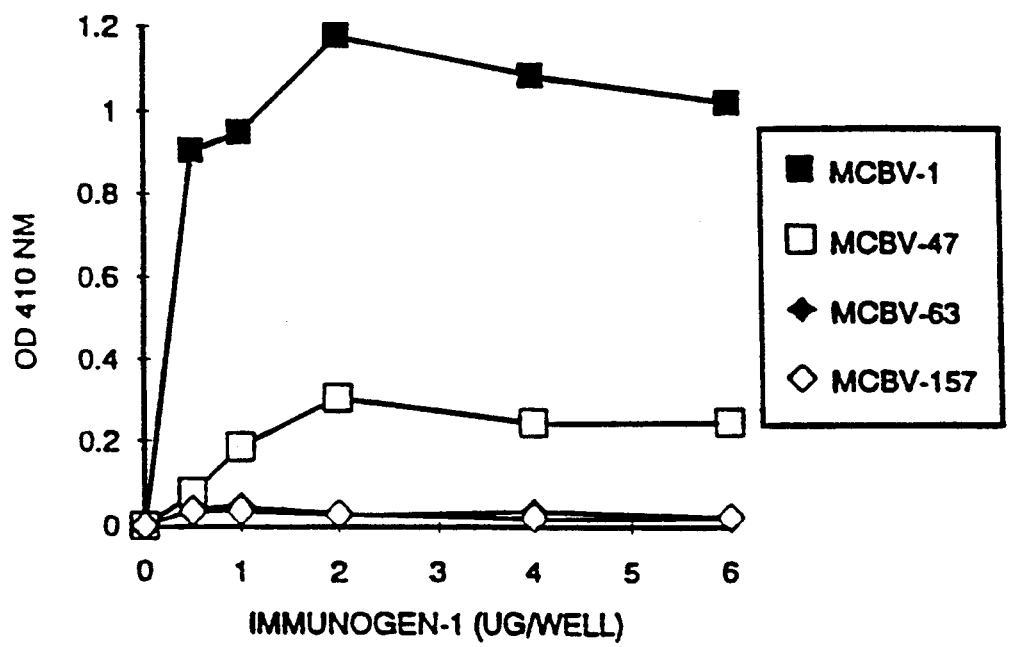
FIG. 4 shows an ELISA for BV-araU using MCBV-1, MCBV-47, MCBV-63 and MCBV-157.

MCBV-1, MCBV-47, MCBV-63 and MCBV-157 could be used to develop heterogeneous non-isotopic solid phase immunoassays. The binding of each monoclonal antibody to immobilized immunogen-1 or immunogen-2 was demonstrated by ELISA (FIGS. 4 A, B). MCBV-1 recognized BV-araU conjugated to thyroglobulin (immunogen-1) (FIG. 4A). Based on ELISA, MCBV-47 also weakly recognizes this form of BV-araU. Maximum binding of MCBV-1 was reached at 2 μg immunogen-1 per well.

Figure 4B:
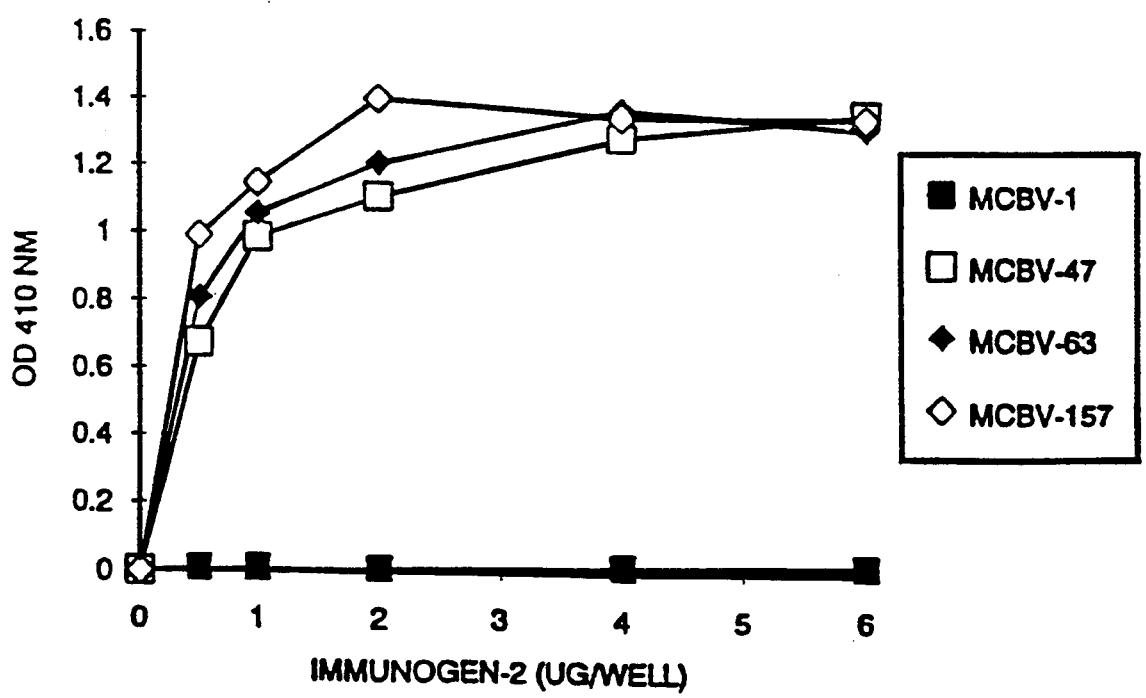

MCBV-47, MCBV-63 and MCBV-157 all recognized BV-araU conjugated to immunogen-2 (FIG. 4B). Optimal binding was reached at approximately 2 μg immunogen-2/well for MCBV-157 and 4 μg immunogen-2/well for MCBV-47 and MCBV-63. The immunogen specificity for each monoclonal antibody as judged by ELISA appears to be similar to the radiolabel specificity demonstrated by RIA.

DETAILED DESCRIPTION OF THE DRAWINGS

FIG. 1: Radioimmunoassay standard curves for MCBV-1, MCBV-47, MCBV-63 and MCBV-157. The $ED_{50}$ for each standard curve was calculated using ISO-DATA 500/100 software as described above.

FIG. 2: Standard curve for BV-araU using radiolabel-3 and ascites fluid containing MCBV-47.

FIG. 3: Cross-reactivity (%) of MCBV-1, MCBV-47, MCBV-63 and MCBV-157 with a major metabolite of BV-araU, 5-bromovinyluracil, and other structurally similar compounds as judged by radioimmunoassay.

FIG. 4: Enzyme-linked immunosorbant assay (ELISA) for BV-araU using MCBV-1, MCBV-47, MCBV-63 and MCBV-157. Immunogen-1 (FIG. 4A) and immunogen-2 (FIG. 4B) were bound to microtiter plate wells at various protein concentrations and the presence of BV-araU determined by an indirect non-isotopic assay as described above.

What is claimed is:

1. A hybrid cell line that produces a monoclonal antibody which binds one or more compounds of the formula:

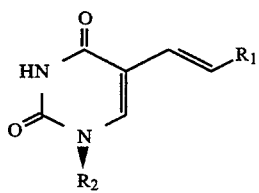

wherein $R_1$ is

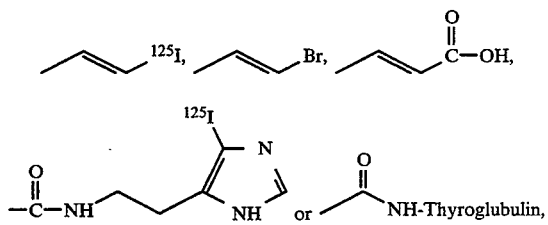

and $R_2$ is

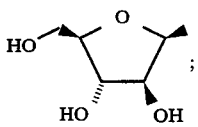

or wherein $R_1$ is

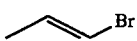

and $R_2$ is H; or wherein $R_1$ is

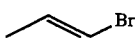

and $R_2$ is

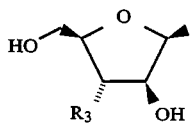

and $R_3$ is —NH-Thyroglobulin or

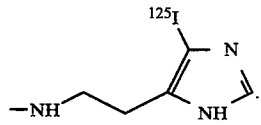

2. The hybrid cell line according to claim 1 wherein the compound is CV-araU.

3. The hybrid cell line according to claim 1 wherein the compound is bromovinyluracil.

4. The hybrid cell line according to claim 1 having the identifying characteristics of a cell line designated HYBV-47.

5. The monoclonal antibody secreted by the hybrid cell line according to claims 2, 3 or 4.

6. The monoclonal antibody secreted by the hybrid cell line according to claim 1.

7. The monoclonal antibody according to claim 6 selected from the group consisting of IgG or IgM.

8. The monoclonal antibody according to claim 6 which is a murine monoclonal antibody.

9. The monoclonal antibody according to claim 6 having the identifying characteristics of a monoclonal antibody designated MCBV-47.

10. The monoclonal antibody according to claims 6 or 9 which has been derivatized.

11. The monoclonal antibody according to claim 10 which has been labelled with a radioisotope.

12. The monoclonal antibody according to claim 11 wherein the radioisotope is selected from the group consisting of $^{125}I$ or $^{131}I$.

13. The monoclonal antibody according to claim 10 which has been conjugated to an enzyme.

14. The monoclonal antibody according to claims 6 or 9 which has been substantially purified.

15. An immunoassay method for detecting the presence of a compound as defined in claim 1 in a sample comprising:

(a) incubating the sample with a monoclonal antibody which binds to the compound; and (b) detecting the presence of immune complexes formed by the compound and the monoclonal antibody.

16. An immunoassay method for quantitatively determining the amount of a compound as defined in claim 1 in a sample comprising:

(a) incubating the sample with a monoclonal antibody which binds to the compound;

(b) determining the amount of immune complexes formed by the compound and the monoclonal antibody; and (c) correlating the amount of immune complexes formed with the amount of the compound present in the sample.

17. The immunoassay method according to claims 15 or 16 which is a radioimmunoassay.

18. The immunoassay method according to claims 15 or 16 which is an enzyme immunoassay.

19. A radioimmunoassay for determining the amount of a compound as defined in claim 1 in a sample comprising:

(a) incubating the sample with a radiolabelled derivative of the compound and a monoclonal antibody which binds the compound;

(b) separating the antibody-bound radiolabelled derivative from the unbound radiolabelled derivative;

(c) measuring the amount of antibody-bound radiolabelled derivative or unbound radiolabelled derivative; and (d) correlating the amount of antibody-bound radiolabelled derivative or unbound radiolabelled derivative with the amount of the compound in the sample.

20. The radioimmunoassay according to claim 19 wherein the antibody-bound radiolabelled derivative is separated from the unbound radiolabelled derivative by precipitating the antibody bound radiolabelled derivative with polyethylene glycol.

21. The radioimmunoassay according to claim 19 wherein the monoclonal antibody is a murine monoclonal antibody.

22. The radioimmunoassay according to claim 19 wherein the radiolabelled derivative is labeled with $^{125}I$.

23. An enzyme immunoassay for determining the amount of a compound as defined in claim 1 in a sample comprising:

(a) incubating the sample with a monoclonal antibody which binds the compound and the compound conjugated to a carrier and immobilized on a solid support;

(b) separating any unbound substances from the solid support;

(c) contacting the solid support with an enzyme-labelled antibody which is capable of binding with the monoclonal antibody which binds the compound;

(d) separating any unbound enzyme-labelled antibody from the solid support;

(e) contacting and incubating the solid support with an enzyme substrate capable of reacting with the enzyme of the enzyme-labelled antibody to produce a detectable reaction product;

(f) measuring the amount of detectable reaction product formed; and (g) correlating the amount of detectable reaction product formed with the amount of the compound in the sample.

24. The enzyme immunoassay according to claim 23 wherein the carrier is thyroglobulin.

25. The enzyme immunoassay according to claim 23 wherein the monoclonal antibody is a murine monoclonal antibody.

26. The enzyme immunoassay according to claim 25 wherein the enzyme-labelled antibody is goat anti-mouse antibody conjugated to horseradish peroxidase.

27. The enzyme immunoassay according to claim 26 wherein the goat anti-mouse antibody is affinity purified.

28. The enzyme immunoassay according to claim 26 wherein the enzyme substrate is hydrogen peroxide and 2,2'-azino-bis(3-ethylbenzthiazoline-6-sulfonic acid).

29. The enzyme immunoassay according to claim 23 wherein the solid support is the inner wall or bottom of a polystyrene microtiter plate well.

30. A hybrid cell line that produces a monoclonal antibody that binds one or more compound selected from:

(a) compounds of the formula

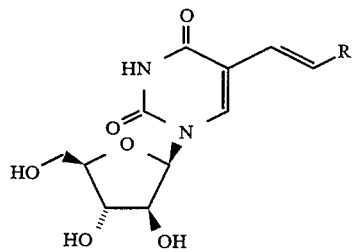

wherein R is —Br,

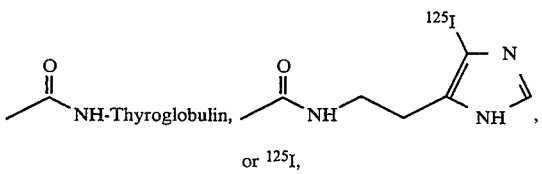

or $^{125}I$, (b) compounds of the formula

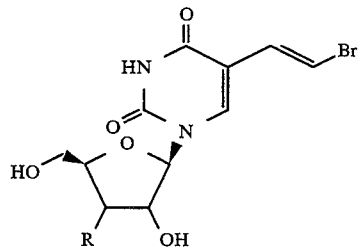

wherein R is NH-thyroglobulin or

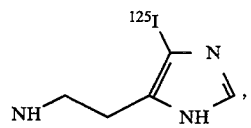

(c) bromovinyluracil, CV-araU, and uracil-$\beta$-D-arabinofuranoside.

* * * * *